(12) United States Patent
Schoenle et al.

(10) Patent No.: US 9,050,414 B2
(45) Date of Patent: Jun. 9, 2015

(54) SYSTEMS AND METHODS FOR MIXING THERAPEUTIC AGENTS BEFORE AND/OR DURING ADMINISTRATION

(75) Inventors: Victor Leo Schoenle, Greenfield, MN (US); Cassandra Ann Piippo Svendsen, Hugo, MN (US); Kristina Tibesar Jensen, Chaska, MN (US); Mark B. Oreschnick, Inver Grove Heights, MN (US); Alyson M. Borrell, Chanhassen, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 230 days.

(21) Appl. No.: 13/029,477

(22) Filed: Feb. 17, 2011

(65) Prior Publication Data
US 2012/0041359 A1 Feb. 16, 2012

Related U.S. Application Data

(60) Provisional application No. 61/306,244, filed on Feb. 19, 2010.

(51) Int. Cl.
| | |
|---|---|
| *B01F 13/08* | (2006.01) |
| *A61M 5/315* | (2006.01) |
| *B01F 11/00* | (2006.01) |
| *B01F 13/00* | (2006.01) |
| *B01F 15/02* | (2006.01) |
| *A61M 25/00* | (2006.01) |

(52) U.S. Cl.
CPC ... *A61M 5/31596* (2013.01); *A61M 2025/0004* (2013.01); *B01F 11/0054* (2013.01); *B01F 13/0023* (2013.01); *B01F 13/0818* (2013.01); *B01F 15/0279* (2013.01)

(58) Field of Classification Search
CPC ............... A61M 2005/31588; A61M 5/31596; A61M 5/31586; A61B 17/8822; B01F 15/0278; B01F 15/0279; B01F 13/0023; B01F 11/0054
USPC .......................... 604/82, 89, 91, 218, 236, 238
See application file for complete search history.

(56) References Cited

U.S. PATENT DOCUMENTS

| | | | |
|---|---|---|---|
| 4,700,705 A | 10/1987 | Kensey et al. | |
| 4,747,821 A | 5/1988 | Kensey et al. | |
| 4,790,813 A | 12/1988 | Kensey | |
| 4,950,238 A | 8/1990 | Sullivan | |
| 5,021,044 A | 6/1991 | Sharkawy | |
| 5,261,877 A | 11/1993 | Fine et al. | |
| 5,336,178 A | 8/1994 | Kaplan et al. | |
| 5,423,744 A | 6/1995 | Gencheff et al. | |

(Continued)

OTHER PUBLICATIONS

International Search Report from related PCT application No. PCT/US2011/025379, Jun. 20, 2011.

*Primary Examiner* — Theodore Stigell
*Assistant Examiner* — Benjamin Koo
(74) *Attorney, Agent, or Firm* — Winthrop & Weinstine, P.A.

(57) ABSTRACT

The invention provides systems and methods for mixing of therapeutic agents before and/or during the localized application of the therapeutic agents. Most preferably, the present invention provides systems and methods for mixing of therapeutic agents before and/or during administration of the agents within a biological lumen. Various embodiments of the present invention comprise systems and methods for inducing a mixing state in the therapeutic agents, thereby inducing and/or maintaining homogeneity of the agents before and/or during localized delivery.

13 Claims, 6 Drawing Sheets

(56) References Cited

U.S. PATENT DOCUMENTS

| | | | |
|---|---|---|---|
| 5,599,306 A | 2/1997 | Klein et al. | |
| 5,611,775 A | 3/1997 | Machold et al. | |
| 5,626,562 A | 5/1997 | Castro | |
| 5,685,847 A | 11/1997 | Barry | |
| 5,713,863 A | 2/1998 | Vigil et al. | |
| 5,779,721 A | 7/1998 | Nash | |
| 5,833,658 A | 11/1998 | Levy et al. | |
| 5,865,794 A | 2/1999 | Castro | |
| 5,879,361 A | 3/1999 | Nash | |
| 5,899,882 A | 5/1999 | Waksman et al. | |
| 6,048,332 A | 4/2000 | Duffy et al. | |
| 6,183,487 B1 | 2/2001 | Barry et al. | |
| 6,478,778 B1 | 11/2002 | Jacobsen et al. | |
| 6,491,938 B2* | 12/2002 | Kunz et al. | 424/423 |
| 6,537,195 B2 | 3/2003 | Forman | |
| 6,544,229 B1* | 4/2003 | Danby et al. | 604/154 |
| 6,569,147 B1 | 5/2003 | Evans et al. | |
| 6,595,388 B2* | 7/2003 | Mizutani et al. | 222/1 |
| 6,599,267 B1 | 7/2003 | Ray et al. | |
| 6,638,246 B1 | 10/2003 | Naimark et al. | |
| 6,645,135 B1 | 11/2003 | Bhat | |
| 6,659,996 B1 | 12/2003 | Kaldany | |
| 6,716,190 B1 | 4/2004 | Glines et al. | |
| 6,764,461 B2 | 7/2004 | Mickley et al. | |
| 6,830,577 B2 | 12/2004 | Nash et al. | |
| 6,843,797 B2 | 1/2005 | Nash et al. | |
| 7,179,251 B2 | 2/2007 | Palasis | |
| 7,364,585 B2 | 4/2008 | Weber | |
| 7,517,338 B2 | 4/2009 | Freyman et al. | |
| 7,524,103 B2* | 4/2009 | McGill et al. | 366/189 |
| 2002/0198550 A1 | 12/2002 | Nash et al. | |
| 2004/0158136 A1 | 8/2004 | Gough et al. | |
| 2005/0107738 A1 | 5/2005 | Slater et al. | |
| 2005/0171476 A1* | 8/2005 | Judson et al. | 604/131 |
| 2005/0240146 A1 | 10/2005 | Nash et al. | |
| 2005/0251106 A1 | 11/2005 | Cervantes et al. | |
| 2006/0190022 A1 | 8/2006 | Beyar et al. | |
| 2006/0253069 A1 | 11/2006 | Li et al. | |
| 2006/0259005 A1 | 11/2006 | Konstantino et al. | |
| 2007/0244429 A1 | 10/2007 | Nguyen et al. | |
| 2007/0299392 A1 | 12/2007 | Beyar et al. | |
| 2008/0058763 A1 | 3/2008 | Boland et al. | |
| 2008/0077165 A1 | 3/2008 | Murphy | |
| 2008/0097499 A1 | 4/2008 | Nash et al. | |
| 2008/0118561 A1 | 5/2008 | Nugent et al. | |
| 2008/0188926 A1 | 8/2008 | Rea | |
| 2008/0195042 A1 | 8/2008 | Weber | |
| 2008/0287911 A1 | 11/2008 | El-Nounou et al. | |
| 2008/0300540 A1* | 12/2008 | Lewis | 604/114 |
| 2008/0300604 A1* | 12/2008 | Lu et al. | 606/94 |
| 2009/0081296 A1 | 3/2009 | Humes et al. | |
| 2009/0105687 A1 | 4/2009 | Deckman et al. | |
| 2010/0094320 A1 | 4/2010 | Arat et al. | |

\* cited by examiner

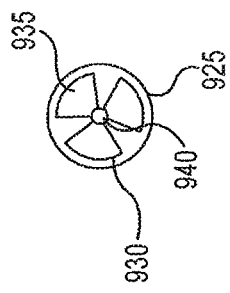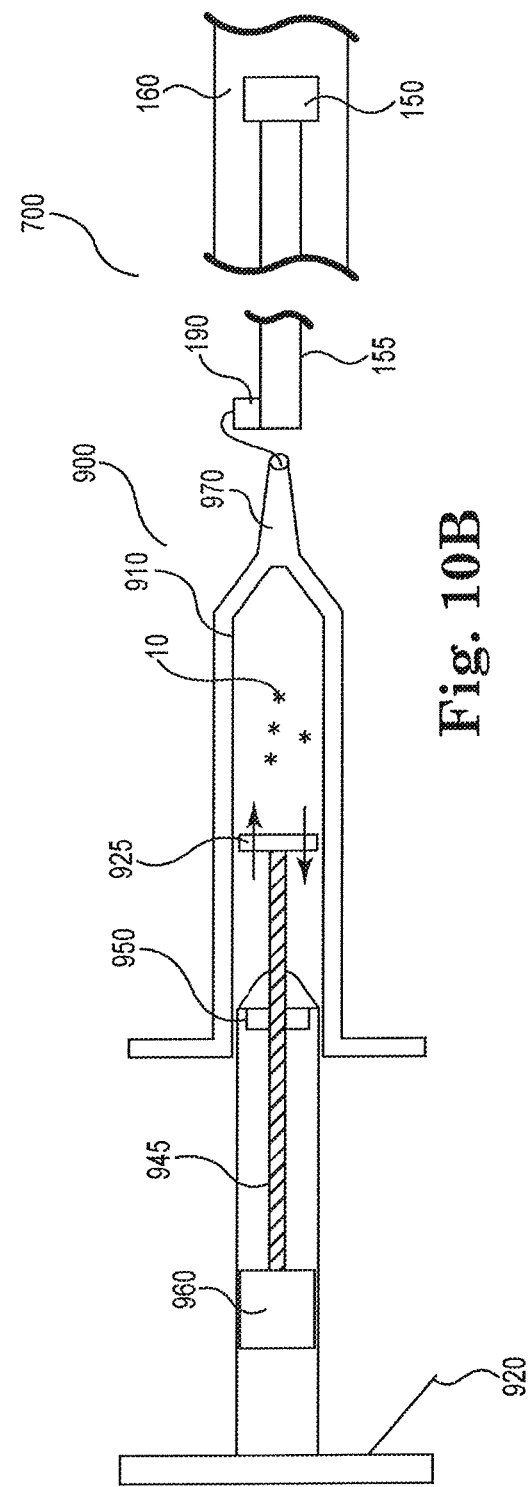

SYSTEMS AND METHODS FOR MIXING THERAPEUTIC AGENTS BEFORE AND/OR DURING ADMINISTRATION

BACKGROUND OF THE INVENTION

1. Field of the Invention

The invention relates to systems and methods for mixing therapeutic cells before and/or during localized delivery, preferably to a biological lumen.

2. Description of the Related Art

A variety of techniques and instruments have been developed for use in the removal or repair of tissue in biological conduits, e.g., without limitation, blood vessels and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes, leg pain and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The disclosure of U.S. Pat. No. 6,494,890 is hereby incorporated by reference in its entirety.

Another method of treatment of occluded biological lumens, e.g., vessels, may include the use of stents. Stents may be placed at the site of a stenosis and expanded to widen the lumen, remaining in position as an implant.

No matter the technique used to open an occluded biological lumen, e.g., blood vessel, and restore normal fluid flow therethrough, one problem remains: restenosis. A certain percentage of the treated conduits and vessels will reocclude (restenose) after a period of time; occurring in as many as 40-50% of the cases. When restenosis does occur, the original procedure may be repeated or an alternative method may be used to reestablish fluid, e.g., blood, flow.

The relevant commonality shared by each of the above treatment methods is that each one results in some trauma to the biological lumen wall. Restenosis occurs for a variety of reasons; each involving trauma. Small clots may form on the wall. Small tears in the wall expose the blood to foreign material and proteins which are highly thrombogenic. Resulting clots may grow gradually and may even contain growth hormones released by platelets within the clot. Moreover, growth hormones released by other cells, e.g., macrophages, may cause smooth muscle cells and fibroblasts in the affected region to multiply in an abnormal fashion. There may be an injury in the biological lumen wall due to the above methods that results in inflammation which may result in the growth of new tissue.

It is known that certain therapeutic agents may have a positive effect on prevention and/or inhibition of restenosis However, intravenous medications are delivered systemically by vein, or regionally, e.g., through intra-lumen infusion without targeting the subject region. Such unnecessary systemic exposure results with unknown and unnecessary adverse results in regions, tissue, and/or organs that are distant from the region of interest. Clearly, systemic delivery and exposure is not well suited to treatment of diseases or conditions having a single intra-lumen region of interest.

The potential utility of mixing therapeutic agents before or during localized application of a therapeutic dose of the therapeutic agent(s) is not limited to treatment of coronary arteries and may comprise any biological lumen. For example, beyond coronary artery delivery, other sites of atherosclerosis, e.g., renal, iliac, femoral, distal leg and carotid arteries, as well as saphenous vein grafts, synthetic grafts and arteriovenous shunts used for hemodialysis would be appropriate biological conduits for a localized therapeutic substance delivery method and mechanism. Nor is the potential utility limited to blood vessels; any biological lumen having a region of interest amenable to treatment may benefit from such a treatment method and mechanism. Finally, the utility of the various embodiments of the present invention are not limited to application to a biologic lumen or conduit. The present invention may be used in virtually any application whereby mixing of therapeutic agent(s) is desired.

One particular problem with one form of therapeutic agent or substance is the tendency for therapeutic cells, e.g., stem cells, to not remain dispersed within a carrier fluid. This results in a failure to provide a continuous dosing strength as the therapeutic agent comprising cells is administered; some regions will receive relatively small doses of the cells, while other regions may receive a super dosing of the cells. In either case, the therapeutic benefit is not maximized and may be harmful to the patient. The present invention is not, however, limited to the mixing of cells. Other therapeutic agents, including but not limited to mixtures of two or more therapeutic agents, may benefit from the present invention.

The present invention overcomes these deficiencies.

BRIEF SUMMARY OF THE INVENTION

The invention provides systems and methods for mixing of therapeutic agents before and/or during the localized application of the therapeutic agents. Most preferably, the present invention provides systems and methods for mixing of therapeutic agents before and/or during administration of the agents within a biological lumen. Various embodiments of the present invention comprise systems and methods for inducing a mixing state in the therapeutic agents, thereby inducing and/or maintaining homogeneity of the agents before and/or during localized delivery.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

FIG. 10A is a side view of one embodiment of the present invention; and

FIG. 10B is a top view of one embodiment of the present invention.

DETAILED DESCRIPTION OF THE INVENTION, INCLUDING THE BEST MODE

Figure 1:
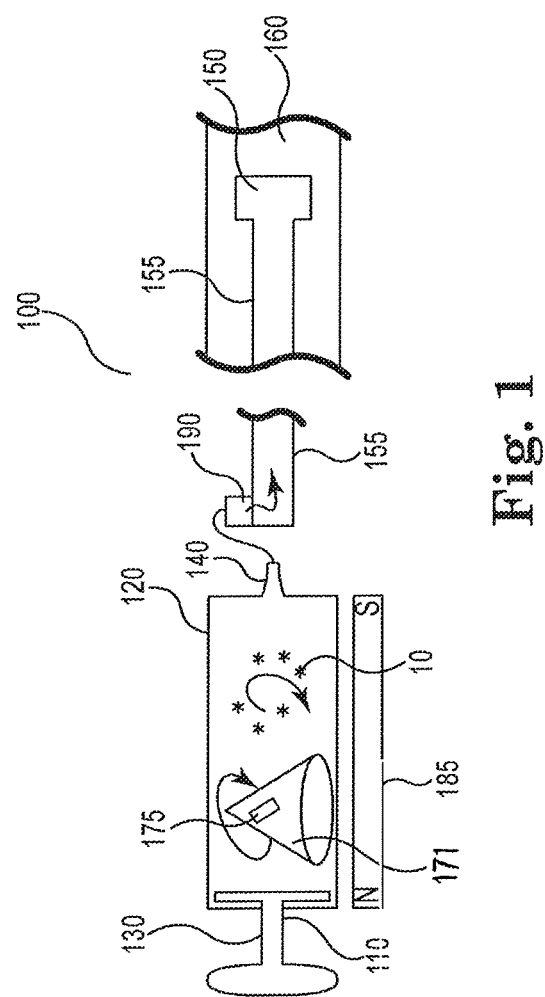
FIG. 1 is a side partial cutaway view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

For the purposes of the present invention, the following terms and definitions apply:

"Bodily disorder" refers to any condition that adversely affects the function of the body including but certainly not limited to regenerative medicine.

The term "treatment" includes prevention, reduction, delay, stabilization, and/or elimination of a bodily disorder, e.g., a vascular disorder or regenerative medicinal techniques using for example stem cells. In certain embodiments, treatment comprises repairing damage cause by the bodily, e.g., vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and minichromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha. and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

Therapeutic agents further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin anticodies, anti-platelet receptor antibodies, aspirin, dipyridamole, protamine, hirudin, prostaglandin inhibitors, platelet inhibitors and tick antiplatelet peptides; vascular cell growth promotors such as growth factors, Vascular Endothelial Growth Factors, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, medically therapeutic substances administered to a procedurally traumatized, e.g., by an angioplasty or atherectomy procedure, mammalian vessel to inhibit restenosis, e.g., a cytoskeletal inhibitor or a smooth muscle inhibitor, including, for example, taxol and functional analogs, equivalents or derivatives thereof such as taxotere, paclitaxel, Abraxane™, Coroxane™ or a cytochalasin, such as cytochalasin B, cytochalasin C, cytochalasin A, cytochalasin D, or analogs or derivatives thereof.

Additional specific examples of "therapeutic agents" that may be mixed before and/or during administration to a biological lumen using various embodiments of the present invention comprise, without limitation:
L-Arginine;
Adipose Cells;
Genetically altered cells, e.g., seeding of autologous endothelial cells transfected with the beta-galactosidase gene upon an injured arterial surface;
Erythromycin;
Penicillin:
Heparin;
Aspirin;
Hydrocortisone;
Dexamethasone;
Forskolin;
GP IIb-IIIa inhibitors;
Cyclohexane;
Rho Kinsase Inhibitors;
Rapamycin;
Histamine;
Nitroglycerin;
Vitamin E;
Vitamin C;
Stem Cells;
Growth Hormones;
Hirudin;
Hirulog;
Argatroban;
Vapirprost;
Prostacyclin;
Dextran;
Erythropoietin;
Endothelial Growth Factor;
Epidermal Growth Factor;
Core Binding Factor A;
Vascular Endothelial Growth Factor;
Fibroblast Growth Factors;
Thrombin;
Thrombin inhibitor; and
Glucosamine, among many other therapeutic substances.

The therapeutic agent mixing systems and methods of the present invention can be used to mix the therapeutic agent before application or delivery to treat any bodily disorder requiring or desiring mixing of the therapeutic agent(s) before and/or during the delivery or administration of the agent(s). Such bodily disorder comprises, without limitation, any bodily disorder within any biological lumen where a catheter can be inserted including any surface within the lumen. Such biological lumen includes, inter alia, blood vessels, e.g., coronary and peripheral vessels, urinary tract, coronary vasculature, esophagus, trachea, colon, and biliary tract.

The therapeutic agent mixing systems and methods of the present invention may be employed before and/or during delivery of the therapeutic agent to treat any biological disorder, including a biological disorder treated within the biological lumen. Moreover, as described in commonly assigned application Ser. No. 13/026,567, the therapeutic agent(s) may be loaded on the application device on a distal location for delivery of the agent(s) to a biological lumen in order to prevent shearing stress and wasting. Further application systems and methods are described in commonly assigned application Ser. No. 13/027,391, including proximal loading and delivery of therapeutic agent(s) to a biological lumen. Application Ser. Nos. 13/026,567 and 13/027,391 are both hereby incorporated in their entirety by reference.

Thus, the therapeutic agent mixing systems and methods of the present invention may be applied to the delivery systems and methods described in the incorporated applications, or to alternative delivery systems and methods for delivering therapeutic agent(s) to treat a bodily disorder, preferably but not limited to a bodily disorder within a biological lumen.

In the preferred case, a catheter will be inserted into a patient's biological lumen, e.g., an artery, with means for delivering therapeutic agent(s) to the lumen as described, inter alia, in application Ser. Nos. 13/026,567 and 13/027,391 or other known means. In some case, the therapeutic agents will be preloaded in a distal region of the catheter or a delivery sheath disposed within the catheter or other distal delivery means. In other cases, the therapeutic agent will be administered by the operator on the proximal end of the catheter, the therapeutic agent traveling the length of the catheter to reach the delivery means. Such delivery means for delivering therapeutic agent(s) to the lumen will be referred to herein as distal therapeutic agent delivery means and include, without limitation, inflatable balloons, stents, delivery sheaths, delivery devices comprising holes or pores through which the therapeutic agent(s) is delivered, either under pressure or as a result of centrifugal force generated during high-speed rotation. Other distal therapeutic agent delivery means may occur to the skilled artisan, each such distal therapeutic agent delivery means is within the scope of the present invention.

FIG. 1 illustrates one system for mixing at least one therapeutic agent before and/or during delivery of the agent(s) to a distal therapeutic agent delivery means. System 100 comprises a syringe 110 comprising a hollow body 120 for storing the therapeutic agent(s) 10 therein to be delivered with a plunger 130 translatable therethrough and a distal port 140, wherein translating the plunger 130 through hollow body 120 and against the stored therapeutic agent(s) pressures the therapeutic agent(s) 10 to move out of the hollow body 120 through distal port 140 as is well known in the art. Ultimately, as described supra, the therapeutic agent(s) are delivered to the distal therapeutic agent delivery means 150 via the lumen of delivery sheath 155 whereby the therapeutic agent(s) 10 is delivered to the biological lumen 160.

An internal mixer 171 comprising a metallic member 175, preferably steel is disposed within hollow body 120. An external rotating magnet 185, disposed adjacent the hollow body 120, and external to the hollow body 120, is provided, wherein the metallic member 175 is magnetically coupled to the external rotating magnet 185, whereby movement of the external rotating magnet 185 induces movement in the internal mixer 171, comprising the metallic member 175. The internal mixer 171 comprises a diameter that is less than the interior diameter of hollow body 120 and a shape that allows movement of the internal mixer 171, e.g., rotation, within the hollow body 120 when actuated by the external rotating magnet 185. This actuation of the internal mixer 171, results when the external rotating magnet 185 may be rotated radially around the hollow body 120 of syringe 110, though other movement pattern of the external rotating magnet 185 may be recognized by the skilled artisan; each such movement pattern is within the scope of the present invention. Moreover, this rotation and/or movement can, as the skilled artisan will readily recognize, be accomplished either by mechanical means or electrically driven, e.g., by use of an electromagnet. The rotation of the external rotating magnet 185 may be continuous or intermediate, depending on the characteristics of the particular therapeutic agent(s) 10 in hollow body 120.

Thus, the internal mixer 171 and the therapeutic agent(s) 10 in hollow body 120 may be actuated into a mixing state by actuation of the rotation of external rotating magnet 185 at any point before or during the procedure to deliver the therapeutic agent(s) 10 to the biological lumen 160 using the distal therapeutic agent delivery means 150. Generally, it may be preferred to actuate the therapeutic agent(s) 10 into a mixing state to induce and/or maintain the homogeneity of the agent(s) 10 at some point before activating the plunger 130 to cause the mixing therapeutic agent(s) 10 out of distal port 140 into, e.g., proximal port 190 and the lumen of delivery sheath 155 and to distal therapeutic agent delivery means 150. Such mixing, or maintenance of the mixing state, may be sustained during the process of moving the therapeutic agent(s) out of the hollow body 120 through distal port 140 via proximal port 190 to maximize the mixing of the agent(s) 10 throughout the process.

Figure 2:
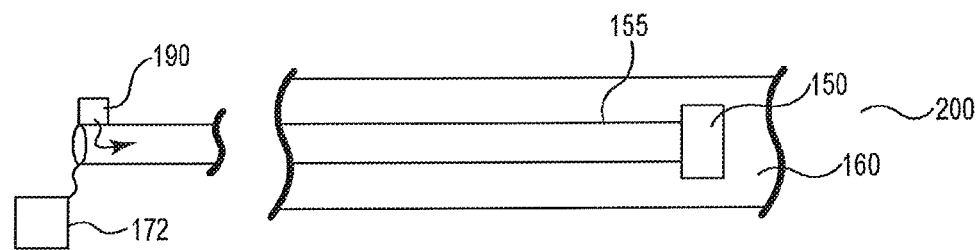
FIG. 2 is a side partial cutaway view of one embodiment of the present invention.

Turning now to FIG. 2, another system 200 for mixing at least one therapeutic agent before and/or during delivery of the agent(s) 10 to a distal therapeutic agent delivery means 150 within a biological lumen 160 is presented. System 200 comprises delivery sheath 155 having a lumen therethrough, positioned within the patient's biological lumen 160, with distal therapeutic agent delivery means 150 positioned near the therapeutic point of interest in lumen 160 for delivery of the therapeutic agent(s) 10 thereto. Therapeutic agent(s) 10 is injected into lumen of delivery sheath 155 at, e.g., a proximal port 190, where the agent(s) 10 may be urged distally down lumen of delivery sheath 155. The mixing system 100 of FIG. 1, may be used, e.g., to achieve the injection of agent(s) 10 into proximal port 190. Since the agent(s) 10 may be resident within lumen of delivery sheath 155 for a period of time which may result in agent(s) 10 becoming less homogeneous over time spent therein, a mixing state of the agent(s) 10 while in the lumen of the delivery sheath 155 is desirable to maintain the homogeneity of the agent(s) 10. Such a mixing state may be achieved by application of ultrasonic energy provided at the proximal end of delivery sheath 155 by an ultrasonic generator 172 which provides relatively low frequency energy, e.g., within the range of 10 k to 400 khz. Thus, turning the ultrasonic generator 172 will subject the delivery sheath 155 and its contents, comprising the at least one therapeutic agent 10, within the lumen of sheath 155 to vibrational energy. This vibrational energy mixes the therapeutic agent(s) 10 along the passage from proximal port 190, through lumen of delivery sheath 155 and to distal therapeutic agent delivery means 150 for delivery to biological lumen 160. Other mechanisms for inducing mixing state by vibrating the sheath 155 and its contents therein may present themselves to the skilled artisan; each such mechanism is within the scope of the present invention.

Figure 3:
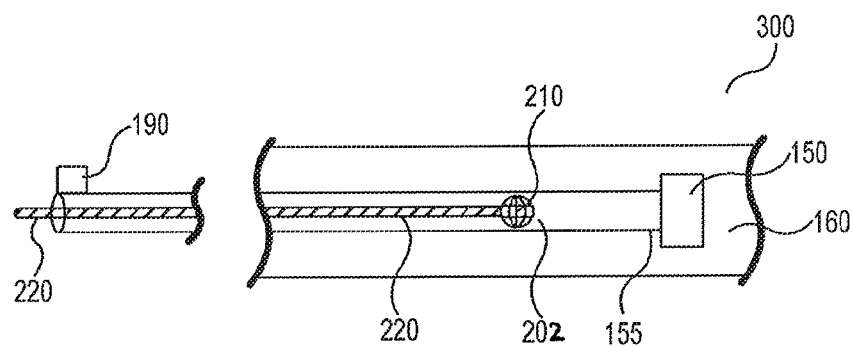
FIG. 3 is a side partial cutaway view of one embodiment of the present invention.

FIG. 3 illustrates another system 300 for mixing at least one therapeutic agent before and/or during delivery of the agent(s) 10 to a distal therapeutic agent delivery means 150 within a biological lumen 160. Delivery sheath 155 is filled with the desired therapeutic amount of at least one therapeutic agent 10 using, e.g., proximal port 190. The mixing system 100 of FIG. 1, may be used, e.g., to achieve the injection of homogeneously mixed agent(s) 10 into proximal port 190. Alternatively, a distal loading of a cell cassette or equivalent may be used to preload and provide the therapeutic agent(s) 10 to lumen of delivery sheath 155.

When therapeutic agent(s) 10 is within lumen of delivery sheath 155, wherein delivery sheath 155 is positioned within biological lumen 160 of patient with distal therapeutic agent delivery means 150 positioned near the therapeutic region of interest, the agent(s) 10 may require a mixing state to remain homogeneous. To achieve and/or maintain the mixing state and homogeneity of agent(s) 10 while resident in lumen of sheath 155, system 300 comprises a hollow ball 202 comprising a plurality of circumferential structures 210, with space therebetween to allow flow and movement of agent(s) 10 therebetween and therethrough. The arrangement of circumferential structures 210 may comprise a vertical and horizontal matrix as illustrated in FIG. 3. Other circumferential structure 210 arrangements may present themselves to the skilled artisan, each arrangement is within the scope of the present invention.

Fixedly connected to at least one of the circumferential structures 210 is an elongated, flexible rod or wire 220. Rod 220 extends through lumen of delivery sheath 155 to the proximal end of the sheath 155 where the operator may slidably and axially translate the rod 220, and therefore the hollow ball 202 within the lumen of delivery sheath 155. As the hollow ball 202 translates through the therapeutic agent(s) within lumen of sheath 155, the agent(s) 10 flow around and through the hollow ball 202 and its circumferential structures 210, creating a mixing state and inducing and/or maintaining homogeneity of the therapeutic agent(s) 10 as they move through the sheath 155 to distal therapeutic agent delivery means 150 for delivery to biological lumen 160.

Figure 4:
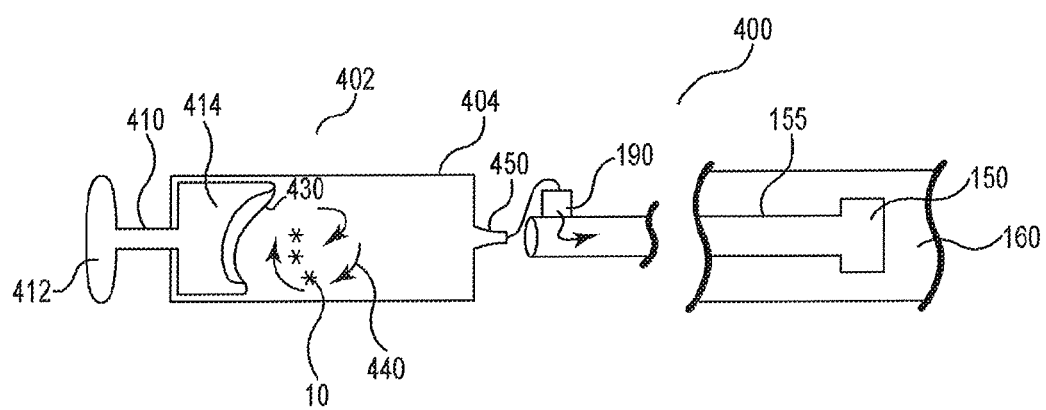
FIG. 4 is a side partial cutaway view of one embodiment of the present invention.

FIG. 4 illustrates one embodiment of a system 400 for mixing at least one therapeutic agent before and/or during delivery of the agent(s) 10 to a distal therapeutic agent delivery means 150 within a biological lumen 160. In this embodiment, syringe 402 comprises a hollow body 404 and a plunger 410 which comprises a plungeable handle 412 and a plunging body 414, the plunging body 414 disposed within hollow body 404 and comprising curvilinear distal surface 430. Curvilinear distal surface 430 comprises a curvilinear profile as illustrated to induce eddy currents 440 swirling distally ahead of the distally advancing plunger 410 and its distal surface 430. In this way, the therapeutic agent(s) 10 in the region of induced eddy currents 440 are in a mixing state, thereby homogenizing the agent(s) 10. The syringe 402 may comprise a distal outflow port 450 through which the homogenized agent(s) 10 may be pressured out of hollow body 404 and ultimately to a distal therapeutic agent delivery means 150 positioned within a patient's biological lumen 160. As illustrated, proximal delivery port 190 may interface with syringe's distal outflow port 450, thereby allowing the flowing homogenized therapeutic agent(s) 10 to move through port 450 and into port 190. From port 190, which is in fluid communication with the lumen of delivery sheath 155, the therapeutic agent(s) 10 move into and distally through lumen of delivery sheath 155 and into distal therapeutic agent delivery means 150 for delivery to biological lumen 160. Alternatively, the agent(s) 10 may be moved through syringe's distal port 450 into a distal loading within delivery sheath 155 or within distal delivery means 150 for subsequent movement into distal therapeutic agent delivery means 150 and delivery to biological lumen 160.

Figure 5:
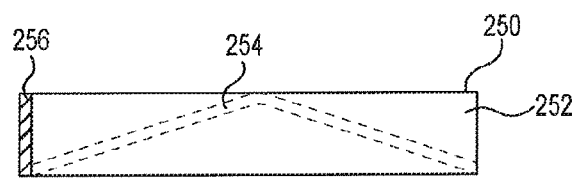
FIG. 5 is a side view of one embodiment of the present invention.
Figure 6:
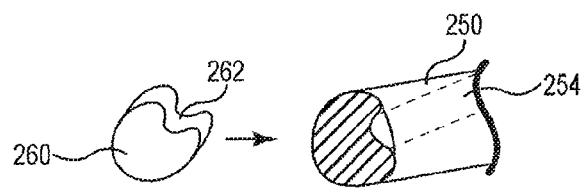
FIG. 6 is a side partial cutaway view of one embodiment of the present invention.
Figure 7:
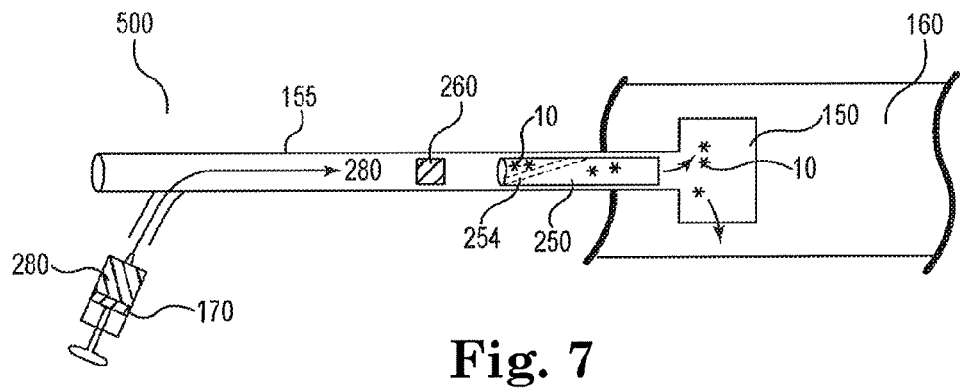
FIG. 7 is a side view of one embodiment of the present invention.

Turning now to FIGS. 5-7, another embodiment of a system 500 for mixing at least one therapeutic agent before and/or during delivery of the agent(s) 10 to a distal therapeutic agent delivery means 150 within a biological lumen 160 is provided. System 500 comprises a therapeutic agent delivery sheath 155 comprising a lumen and a therapeutic agent cassette 250 in communication with lumen of sheath 155 and which seeks to reduce shear stress and damage, eliminate waste and isolate therapeutic agents. The therapeutic agent cassette 250 may comprise a flexible polymer tube 252 having a lumen therethrough comprising a diameter and a raised spiral guide 254 defined within lumen. Cassette 250 may be preloaded with a predetermined amount of therapeutic agent(s) 10 and further comprises a proximal end through which pressure may be applied to cause the therapeutic agent(s) 10 to move out of the distal end of cassette 250 and into the distal therapeutic agent delivery means 150 for delivery to the biological lumen 160. Application of pressure may comprise an isolation plug 260 inserted and translatable through lumen of delivery sheath 155 which may be moved by a pressuring saline 280 injection with a syringe device 170 as illustrated or, alternatively, by a mechanical means such as a wire that is pushed distally against isolation plug 260 through the lumen of sheath 155. Isolation plug 260 comprises a guide region 262, plug 260 therefore comprising a shape that is complementary to the lumen of cassette 250 comprising raised spiral guide 254 of cassette 250.

The cassette 250 may comprise a membrane seal on proximal and distal ends of the lumen of cassette 250 to prevent egress of the therapeutic agent(s) 150 contained therein and to prevent contamination of the agent(s) 10. The membrane seals may be broken by the application of pressure, either by saline 280 pressure and movement of the isolation plug 260 or by mechanical movement of same.

Movement of the isolation plug 260 within lumen of cassette 250 causes translational and rotational engagement of raised spiral guide 254 of cassette 250 with guide region 262 of isolation plug. Such translational and rotational engagement and movement of isolation plug 260 results in a mixing state for the therapeutic agent(s) 10 within the lumen of cassette 250, thereby establishing, restoring and/or maintaining the homogeneity of the agent(s) 10. The spiral guide 254 is illustrated as a raised element, with guide region 262 of isolation plug 260 complementarily recessed to fit. The opposite situation may also be employed, wherein the spiral guide 254 comprises a recessed spiral guide region with isolation plug's guide region 262 comprising a raised complementary shaping to engage recessed spiral guide region.

Proximal end of cassette 250 may further comprise, in certain embodiments a connection means 256, e.g., threads or a snapping connection, for connecting with the distal end of the delivery sheath 155 prior to insertion into patient. In this case, the cassette 250 and its load of therapeutic agent(s) 10 will be preloaded ahead of the procedure. Alternatively, one embodiment of the distal cassette 250 may comprise the lumen of delivery sheath 155 having a preformed distal seating within which the preloaded cassette 250 is inserted and which may be removably covered by a sheath cover that is axially moveable, i.e., able to expose and/or cover the installed or inserted cassette 250. The isolation plug 160 may then be pressured distally against the proximal membrane, bursting both the proximal and distal membranes and causing the therapeutic agent(s) 10 to flow into the distal therapeutic agent delivery means 150 and delivered to the biological lumen 160.

Figure 8:
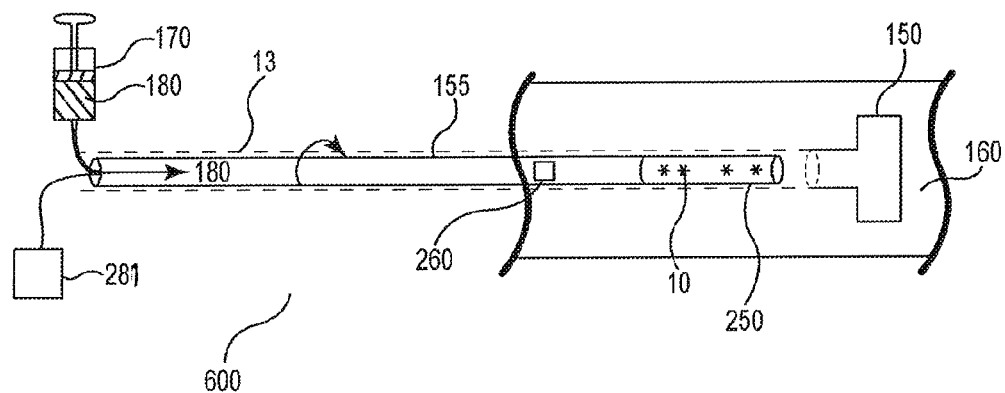
FIG. 8 is a side view of one embodiment of the present invention.

Turning to FIG. 8, another embodiment of a system 600 for mixing at least one therapeutic agent before and/or during delivery of the agent(s) 10 to a distal therapeutic agent delivery means 150 within a biological lumen 160 is illustrated. In this embodiment, catheter 13 is positioned in biological lumen 160, catheter 13 having a lumen therethrough, within which delivery sheath 155 is slidably and rotatably disposed. The therapeutic agent(s) 10 are placed into the system 600 through use of the cassette 250 and methods of preloading described in connection with FIGS. 5-7. In addition, the syringe 170 for saline injection 180 within lumen of sheath 155 to pressure isolation plug 260 into and through lumen of cassette 250 may be provided to deliver agent(s) 10 into lumen of catheter 13 distal to cassette 250, into distal therapeutic agent delivery means 150 and into biological lumen 160. In this system 600, the spiral guide 254 of cassette 250 and guide region 262 of isolation plug 260 may be present, though in alternate embodiments, the spiral guide 254 and guide region 262 are not present.

System 600 further comprises a slow rotational speed motor 281, operatively connected with delivery sheath 155 and which causes, when actuated, a slow rotation of delivery sheath 155. When the therapeutic agent(s) 10 are within sheath 155, they are thus induced to a mixing state and regain or maintain homogeneity.

An alternative to the cassette 250 whereby agent(s) 10 are loaded into sheath 155 of system 600 comprises introduction of agent(s) by a syringe at a proximal loading port such as the port 190 described in connection with FIG. 1.

Further alternatives to the flexible tube cassette 250 may comprise the therapeutic agent(s) being frozen in a tubular shape then placed into delivery sheath 155 for thawing and subsequent pressuring with isolation plug 160.

Figure 9:
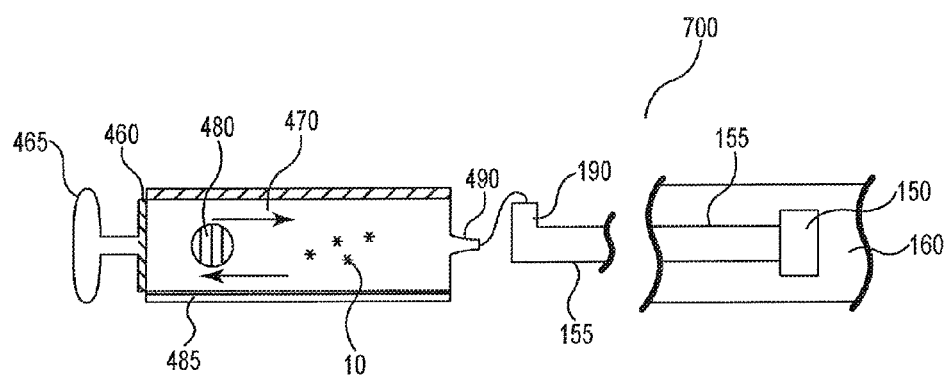
FIG. 9 is a side partial cutaway view of one embodiment of the present invention.

FIG. 9 illustrates another embodiment of a system 700 for mixing at least one therapeutic agent before and/or during delivery of the agent(s) 10 to a distal therapeutic agent delivery means 150 within a biological lumen 160. In this system 700, a syringe 460 comprising a plunger 465 and a hollow body 470 as is commonly known in the art. A metallic ball 480, preferably steel, is provided within hollow body 470 and sized with a diameter that is smaller than the diameter of the hollow body 470, to allow the ball 480 rolling movement within hollow body 470. Disposed outside and adjacent hollow body 470 is a rotating magnet 485, rotatable by mechanical or electrical means that will be readily apparent to the skilled artisan. Actuation of the rotating means induces the metallic ball 480, magnetically coupled with rotating magnet 485, to roll distally and proximally within hollow body 470, thereby inducing a mixing state for the therapeutic agent(s) 10 therein and homogenizing agent(s) 10. Actuating plunger 465 after the induction of mixing state results in agent(s) 10 moving out of distal port 490 of syringe 460 and into, e.g., a proximal port 190 and into lumen of delivery sheath 155 which delivers the agent(s) to distal delivery means 150 for delivery to biological lumen 160.

FIGS. 10A and 10B provide an embodiment of a syringe 900 for mixing at least one therapeutic agent before and/or during delivery of the agent(s) 10 to a distal therapeutic agent delivery means 150 within a biological lumen 160 via, e.g., a proximal port 190 in fluid communication with lumen of delivery sheath 155. Mixing syringe 900 comprises a hollow body 910, wherein therapeutic agent(s) 10 may be loaded. Syringe 900 further comprises a plunger assembly 920. Plunger assembly comprises a plunging base 925 disposed within hollow body 910 comprising a fan 930 with blades 935 the blades 935 operatively connected with a rotatable central axle 940. Rotatable central axle 940 is, in turn, operatively connected with a threaded shaft 945 that is in threaded communication and connection with threaded block 950. The proximal end of threaded shaft 945 comprises a floating motor 960 mounted thereon, floating motor 960 arranged to actuate rotation of threaded shaft 945 which causes threaded translation of threaded shaft 945 through threaded block 950, and resultant axial translation of fan 930 through the therapeutic agent(s) 10 within hollow body 910. This axial translation of fan 930 results in rotation of fan blades 935, resulting in a mixing state for the therapeutic agent(s) 10 within hollow body 910. As the motor 960 spins, the threaded shaft 945 threadingly translates, e.g., distally through threaded block 950 until resistance is encountered at the distal end of the syringe 900, mixing the therapeutic agent(s) 10 therein to homogeneity. The distal translation of the threaded shaft 945 and the rotating fan blades 935 pressures some of the homogenized therapeutic agent(s) 10 through outflow port 970 and into, e.g., proximal port 190 which is in fluid communication with lumen of therapeutic agent delivery sheath 155 which is in fluid communication with distal therapeutic agent delivery means 150 for delivery to biological lumen 160.

When resistance is encountered by the device at the distal end of hollow body 910, the motor 960 reverses causing a concurrent reversal in the rotational direction of threaded shaft 945. This results in a reversal of the fan blade 935 rotational direction. The reversing threaded shaft 945 proximally up through threaded block 950 and hollow body 910, wherein the fan blades 935 continue to mix and homogenize the remaining therapeutic agent(s) 10 until proximal resistance is encountered at the proximal end of the hollow body 910. At this point, the motor 960, threaded shaft 945 and fan blades 935 again reverse rotational direction, the shaft 945 and fan blades 935 moving distally down through the hollow body 910, again pressuring some of the therapeutic agent(s) 10 out of hollow body through distal port 970, ultimately to be delivered to biological lumen 160.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A system for mixing at least one therapeutic agent before and/or during localized delivery of the at least one therapeutic agent to treat a bodily disorder, comprising a mixing and delivery syringe, wherein the syringe comprises:

a hollow body having a proximal end and a distal end, wherein the at least one therapeutic agent is stored;

a distal port in fluid communication with the distal end of hollow body; and a plunger assembly comprising:
a plunging base disposed within the hollow body;
a fan disposed within the hollow body, the fan comprising rotatable blades extending radially from a rotatable central axle;
a threaded shaft comprising a distal end rotatably coupled with the rotatable central axle for enabling rotational movement of the rotatable blades about the distal end of the threaded shaft;
a threaded block in threaded communication with the threaded shaft; and
a floating motor mounted on a proximal end of the threaded shaft;

wherein,
the motor is configured to rotate the threaded shaft;
the rotation of the threaded shaft in a first direction induces threaded translation of the threaded shaft through the threaded block;
the threaded translation of the threaded shaft induces axial translation of the floating motor, the fan and the plunging base towards the distal end of the hollow body; and
the axial translation of the fan induces the rotational movement of the rotatable blades about the distal end of the threaded shaft, wherein when resistance is encountered at the distal end of the hollow body, the floating motor reverses rotational direction to a second rotational direction, wherein the rotation of the threaded shaft in the second direction induces threaded translation of the threaded shaft through the threaded block and the threaded translation of the threaded shaft induxes axial translation of the floating motor, the fan and the plunging base towards the proximal end of the hollow body, wherein when resistance is encountered at the proximal end of the hollow body, the floating motor reverses rotational direction to the second rotational direction until resistance is encountered at the distal end of the hollow body.

2. The system of claim 1, wherein the bodily disorder is within a vasculature.

3. The system of claim 1, wherein the bodily disorder comprises restenosis.

4. The system of claim 1, wherein the at least one therapeutic agent comprises at least one therapeutic cell.

5. The system of claim 1, wherein the at least one therapeutic agent comprises a cytoskeletal inhibitor.

6. The system of claim 1, wherein the at least one therapeutic agent comprises a smooth muscle inhibitor.

7. The system of claim 1, wherein the rotation of the threaded shaft in a second direction opposite the first direction axially translates the fan and the plunging base towards the distal end of the hollow body.

8. The system of claim 7, wherein the rotational movement of the fan at least partially mixes the at least one therapeutic agent.

9. The system of claim 8, wherein the axial translation of the fan and the plunging base towards the distal end expels at least a portion of the at least one therapeutic agent through the distal port.

10. The system of claim 9, comprising a delivery sheath comprising:
   a distal end; and
   a proximal end in fluid communication with the distal port;
      wherein, the at least one therapeutic agent expelled through the distal port exits through the distal end of the delivery sheath.

11. The system of claim 10, comprising a therapeutic delivery means in fluid communication with the distal end of the delivery sheath, wherein the therapeutic deliver means is selected from the group consisting of: a balloon, a stent, and a delivery apparatus comprising one or more holes through which the homogeneous composition is released.

12. The system of claim 10, wherein the bodily disorder is within a vasulature and wherein the distal end of the delivery sheath is disposed proximate the bodily disorder.

13. The system of claim 7, wherein the rotational movement of the fan mixes the at least one therapeutic agent into a homogeneous composition.

* * * * *